United States Patent
Cullis-Hill (10) Patent No.: US 11,938,146 B2
(45) Date of Patent: *Mar. 26, 2024

(54) TREATMENT FOR CORONAVIRUS INFECTION AND ASSOCIATED CYTOKINE TOXICITY

(71) Applicant: Sydney David Cullis-Hill, Bondi Junction (AU)

(72) Inventor: Sydney David Cullis-Hill, Bondi Junction (AU)

(*) Notice: Subject to any disclaimer, the term of this patent is extended or adjusted under 35 U.S.C. 154(b) by 0 days.

This patent is subject to a terminal disclaimer.

(21) Appl. No.: 18/071,800

(22) Filed: Nov. 30, 2022

(65) Prior Publication Data

US 2023/0201250 A1    Jun. 29, 2023

Related U.S. Application Data

(63) Continuation of application No. 17/910,220, filed as application No. PCT/AU2021/050215 on Mar. 12, 2021.

(30) Foreign Application Priority Data

Mar. 12, 2020 (AU) .............................. 2020900751
Dec. 23, 2020 (AU) .............................. 2020904824

(51) Int. Cl.
*A61K 31/737*  (2006.01)
*A61K 45/06*  (2006.01)
*A61P 31/14*  (2006.01)

(52) U.S. Cl.
CPC ............ *A61K 31/737* (2013.01); *A61K 45/06* (2013.01); *A61P 31/14* (2018.01)

(58) Field of Classification Search
None
See application file for complete search history.

(56) References Cited

U.S. PATENT DOCUMENTS 2,689,848 A * 9/1954 Husemann .......... C08B 37/0057
536/118
5,872,109 A   2/1999 Akima et al.

FOREIGN PATENT DOCUMENTS

| WO | 1994/011006 A1 | 5/1994 |
| WO | 2006/003521 A1 | 1/2006 |
| WO | 2008/144836 A1 | 12/2008 |
| WO | 2009/027057 A1 | 3/2009 |
| WO | 2010/130466 A1 | 11/2010 |
| WO | 2017/009351 A1 | 1/2017 |

OTHER PUBLICATIONS

Lee, Eva, et al. "Antiviral effect of the heparan sulfate mimetic, PI-88, against dengue and encephalitic flaviviruses." Antiviral research 69.1 (2006): 31-38.*
Andrei, Graciela, et al. "Comparative activity of various compounds against clinical strains of herpes simplex virus." European Journal of Clinical Microbiology and Infectious Diseases 11 (1992): 143-151.*
Pluda, James M., et al. "Administration of pentosan polysulfate to patients with human immunodeficiency virus-associated Kaposi's sarcoma." JNCI: Journal of the National Cancer Institute 85.19 (1993): 1585-1592.*
Francis et al. Arthritis and Rheumatism (1989), vol. 32, pp. 608-616.*
Baba et al. Antimicrobial Agents and Chemotherapy (1988), vol. 32, pp. 1742-1745.*
Huang et al., Clinical features of patients infected with 2019 novel coronavirus in Wuhan, China. Lancet. Feb. 15, 2020;395(10223):497-506.
Ianevski et al., Novel activities of safe-in-human broad-spectrum antiviral agents. Antiviral Res. Jun. 2018;154:174-182.
Koenighofer et al., Carrageenan nasal spray in virus confirmed common cold: individual patient data analysis of two randomized controlled trials. Multidiscip Respir Med. Nov. 12, 2014;9(1):57.
Sanden et al., Broad Th2 neutralization and anti-inflammatory action of pentosan polysulfate sodium in experimental allergic rhinitis. Immun Inflamm Dis. Sep. 2017;5(3):300-309.
Vicenzi et al., Coronaviridae and SARS-associated coronavirus strain HSR1. Emerg Infect Dis. Mar. 2004;10(3):413-8.
International Search Report and Written Opinion for Application No. PCT/AU2021/050215, dated Mar. 15, 2021, 12 pages.

* cited by examiner

*Primary Examiner* — Patrick T Lewis (74) *Attorney, Agent, or Firm* — McCarter & English, LLP; Yu Lu (57) ABSTRACT

The present invention relates to novel methods for treating or preventing coronavirus infection and cytokine-associated toxicity, including cytokine toxicity resulting from aberrant activation of the immune system in coronavirus disease or infection, such as those from SARS-CoV-2.

22 Claims, 2 Drawing Sheets

TREATMENT FOR CORONAVIRUS INFECTION AND ASSOCIATED CYTOKINE TOXICITY

RELATED APPLICATIONS

This application is a continuation application of U.S. Ser. No. 17/910,220, filed on Sep. 8, 2022, which is a U.S. National Stage Application filed under 35 U.S.C. § 371(c), based on International Patent Application No. PCT/AU2021/050215, filed on Mar. 12, 2021, which claims priority to and the benefit of the filing dates of Australian Patent Application Nos. 2020900751, filed on Mar. 12, 2020, and 2020904824, filed on Dec. 23, 2020, the entire contents of each of the above-referenced applications are incorporated herein by reference.

FIELD OF THE INVENTION

The present invention relates to novel methods for treating or preventing coronavirus infection and cytokine-associated toxicity, including cytokine toxicity resulting from aberrant activation of the immune system in coronavirus disease or infection, such as those from SARS-CoV-2.

BACKGROUND OF THE INVENTION

Coronaviruses are a group of viruses that cause diseases in mammals and birds. In humans, coronaviruses cause respiratory tract infections that are typically mild, such as some cases of the common cold (among other possible causes, predominantly rhinoviruses), though rarer forms can be lethal, such as SARS, MERS, and SARS-CoV-2. Symptoms vary in other species: in chickens, they cause an upper respiratory tract disease, while in cows and pigs they cause diarrhoea. There are yet to be vaccines or antiviral drugs to prevent or treat human coronavirus infections.

Coronaviruses constitute the subfamily Orthocoronavirinae, in the family Coronaviridae, order Nidovirales, and realm Riboviria. They are enveloped viruses with a positive-sense single-stranded RNA genome and a nucleocapsid of helical symmetry. The genome size of coronaviruses ranges from approximately 27 to 34 kilobases, the largest among known RNA viruses.

In 2020, the world faced an extreme situation of a highly infectious coronavirus (2019-nCoV; SARS-CoV-2) manifesting as a disease termed "COVID-19". SARS-CoV-2 infections globally have exceeded 100 million confirmed cases with more than 2 million deaths to date, across more than 200 countries, areas or territories. COVID-19 manifestations range from mild to severe life-threatening with a substantial mortality rate.

It is likely that Angiotensin Converting Enzyme 2 (ACE2) is the receptor target for SARS-CoV-2. ACE2 is an exopeptidase that catalyses the conversion of angiotensin I to the nonapeptide angiotensin or the conversion of angiotensin II to angiotensin. ACE2 has a broad expression profile, being expressed in nearly all human organs to varying degrees. In the respiratory system, ACE2 is mainly expressed on type II alveolar epithelial cells, but is also expressed at lower levels in the oral and nasal mucosa and nasopharynx. ACE2 is also highly expressed on myocardial cells, proximal tubule cells of the kidney, bladder urothelial cells and is abundantly expressed on the enterocytes of the small intestine, especially in the ileum. Consequently, there are multiple sites for potential entry of the SARS-CoV-2 virus Given that the receptor target of SARS-CoV-2 is expressed in multiple different tissue types, COVID-19 disease has been shown to manifest with symptoms that include the intestinal and vascular systems, in addition to the respiratory system. As the disease progresses or worsens, the risk of aberrant inflammation and cytokine storm increases.

Cytokine-associated toxicity, also known as cytokine release syndrome (CRS), is a non-antigen specific toxicity that occurs as a result of high-level immune activation. CRS manifests when large numbers of lymphocytes and/or myeloid cells become activated and release inflammatory cytokines. The result is a potentially fatal immune reaction consisting of a positive feedback loop between cytokines and lymphocytes. In severe cases, the CRS is referred to as a 'cytokine storm', and can occur as a result of coronavirus infection.

Cytokine-associated toxicity has been reported occur in response to a variety of infectious and non-infectious diseases including graft versus host disease (GVHD), acute respiratory distress syndrome (ARDS), sepsis, Ebola, avian influenza, smallpox, and systemic inflammatory response syndrome (SIRS).

There is a need for new or improved treatments for coronavirus infections and/or conditions associated with, or caused by, coronaviruses. Reference to any prior art in the specification is not an acknowledgment or suggestion that this prior art forms part of the common general knowledge in any jurisdiction or that this prior art could reasonably be expected to be understood, regarded as relevant, and/or combined with other pieces of prior art by a skilled person in the art.

SUMMARY OF THE INVENTION

In a first aspect, the present invention provides a method of treating or preventing a coronavirus infection, comprising:
  providing a subject who is suspected of having or at risk of developing a coronavirus infection,
  administering to the subject, a therapeutically effective amount of sulfated polysaccharide or a pharmaceutically acceptable salt thereof,
  thereby treating or preventing coronavirus infection in the subject.

In a further aspect, the present invention provides a method for reducing the severity of a coronavirus infection, the method comprising administering to a subject in need thereof, a therapeutically effective amount of sulfated polysaccharide or a pharmaceutically acceptable salt thereof, thereby reducing the severity of the coronavirus infection in the subject. Preferably the coronavirus infection is an infection with a beta-coronavirus, more preferably an infection with a beta-coronavirus from Lineage B, such as an infection with SARS-CoV or an infection with SARS-CoV-2. More preferably, the infection is an infection with SARS-CoV-2 or a mutated form or variant thereof, including but not limited to mutants D614G, S477N, 20A.EU1, the Danish COVID-19 mink variant, the "UK" variant B 1. 1. 7, the "South African" variant B. 1. 351, the "Brazil" variant P.1 or the "Russian" variant B. 1. 1. 317.

In another aspect, the present invention provides a method of treating and/or preventing a disease associated with, or caused by, a coronavirus, the method comprising administering to a subject in need thereof a therapeutically effective amount of sulfated polysaccharide or a pharmaceutically acceptable salt thereof, thereby treating and/or preventing a disease associated with, or caused by, a coronavirus.

Preferably the disease is associated or caused by a beta-coronavirus, more preferably a beta-coronavirus from Lineage B, such as SARS-CoV or SARS-CoV-2. Most preferably, the disease is associated or caused by SARS-CoV-2 or a mutated form or variant thereof, including but not limited to mutants D614G, S477N, 20A.EU1, or the Danish COVID-19 mink variant. Alternatively, the disease is associated or caused by a beta-coronavirus from Lineage C, optionally MERS-CoV.

The disease associated with or caused by the coronavirus infection may be a respiratory disease, an inflammatory disease (including cytokine-associated toxicity), a cardio-vascular disease or a gastrointestinal disease.

Accordingly, in another aspect, the present invention provides a method of treating and/or preventing a respiratory disease or condition associated with a coronavirus infection, the method comprising administering to a subject in need thereof, a therapeutically effective amount of sulfated polysaccharide or a pharmaceutically acceptable salt thereof, thereby treating and/or preventing a respiratory disease or condition associated with a coronavirus infection. Preferably the respiratory disease or condition is associated with a beta-coronavirus, more preferably a beta-coronavirus from Lineage B, such as SARS-CoV or SARS-CoV-2. Most preferably, the respiratory disease or condition is associated or caused by SARS-CoV-2 or a mutated form or variant thereof, including but not limited to mutants D614G, S477N, 20A.EU1, the Danish COVID-19 mink variant, the "UK" variant B 1. 1. 7, the "South African" variant B. 1. 351, the "Brazil" variant P.1 or the "Russian" variant B. 1. 1. 317.

In this aspect, the respiratory disease or condition may comprise airway inflammation and the method thereby reduces airway inflammation in the subject or improves the ability of the subject to control a respiratory disease or condition during a coronavirus infection.

Further, the present method provides a method of treating or preventing cytokine-associated toxicity caused by or associated with a coronavirus infection, the method comprising:
   providing a subject who is suspected of having coronavirus infection and is at risk of developing or has developed cytokine-associated toxicity,
   administering to the subject, a therapeutically effective amount of a sulfated polysaccharide or a pharmaceutically acceptable salt thereof,
   thereby treating or preventing cytokine-associated toxicity in the subject. Preferably, the cytokine-associated toxicity is associated or caused by a beta-coronavirus, more preferably a beta-coronavirus from Lineage B, such as SARS-CoV or SARS-CoV-2. Most preferably, the disease is associated or caused by SARS-CoV-2 or a mutated form or variant thereof, including but not limited to mutants D614G, S477N, 20A.EU1, or the Danish COVID-19 mink variant. Alternatively, the disease is associated or caused by a beta-coronavirus from Lineage C, optionally MERS-CoV.

In any aspect, treatment of a coronavirus disease comprises treating one or more symptoms associated with infection with a coronavirus or with a disease associated with or caused by coronavirus infection. Accordingly, in still a further aspect, the present invention relates to a method of treating one or more of fever, hypotension, tachycardia, myalgia, headache, vascular inflammation, gastrointestinal inflammation and dysfunction, or inappropriate cytokine release, caused by or associated with a coronavirus infection, the method comprising:
   providing a subject who has or is suspected of having a coronavirus infection, and wherein the individual has or is suspected of having fever, hypotension, tachycardia, myalgia, headache, vascular inflammation, gastrointestinal inflammation and dysfunction, or inappropriate cytokine release induced by the coronavirus,
   administering to the individual, a therapeutically effective amount of sulfated polysaccharide or pharmaceutically acceptable salt thereof,
   thereby treating one or more of fever, hypotension, tachycardia, myalgia, headache, vascular inflammation, gastrointestinal inflammation and dysfunction, or inappropriate cytokine release induced by coronavirus infection. Preferably, the coronavirus infection is an infection with a beta-coronavirus, preferably from an infection with a beta-coronavirus from Lineage B, such as an infection with SARS-CoV or an infection with SARS-CoV-2. Preferably, the coronavirus infection is a SARS-CoV-2 infection, or an infection with a mutated form or variant thereof, including but not limited to mutants D614G, S477N, 20A.EU1, or the Danish COVID-19 mink variant.

In a further aspect, the present invention provides a method of treating cytokine-associated toxicity induced by acute respiratory distress syndrome (ARDS), sepsis, systemic inflammatory response syndrome (SIRS), severe viral infection, pneumonia severe acute respiratory syndrome (SARS), comprising:
   providing an individual who is suspected of having cytokine-associated toxicity induced by acute respiratory distress syndrome (ARDS), sepsis, systemic inflammatory response syndrome (SIRS), severe viral infection, pneumonia severe acute respiratory syndrome (SARS),
   administering to the individual, an amount of sulfated polysaccharide or a pharmaceutically acceptable salt thereof effective to treat the cytokine-associated toxicity,
   wherein the sulfated polysaccharide is selected from the group consisting of pentosan polysulfate, chondroitin sulfate A, chondroitin sulfate B, chondroitin sulfate C, keratan sulfate, heparin, heparan sulfate, dextran polysulfate, fucoidan, lentinan sulfate, mannan sulfate, galactan sulfate, xylomannan sulfate, rhamnan sulfate, curdlan sulfate, or sulfated fucan, and pharmaceutically acceptable salts thereof,
   thereby treating cytokine-associated toxicity in the individual.

The invention also relates to a method of preventing one or more of fever, hypotension, tachycardia, myalgia, headache or inappropriate cytokine release induced by coronavirus infection, including
   providing a subject who is exposed to coronavirus infection, and wherein the subject is at risk of developing fever, hypotension, tachycardia, myalgia, headache or inappropriate cytokine release induced by the exposure,
   administering to the subject, an amount of sulfated polysaccharide or pharmaceutically acceptable salt thereof, effective to prevent one or more of fever, hypotension, tachycardia, myalgia, headache or inappropriate cytokine release,
   thereby preventing fever, hypotension, tachycardia, myalgia, headache or inappropriate cytokine release induced by coronavirus exposure.

It will be appreciated that the methods of the invention extend to the treatment or prevention of a range of disease severity. In certain embodiments, the symptoms are mild such that the subject can be treated at home. In other embodiments, the symptoms are more severe, requiring hospitalisation, or even intensive care unit treatment.

In further aspects of the invention, there is provided a method for preventing or reducing the likelihood of infection (including of severe infection) with a coronavirus. The methods comprise administering a sulfated polysaccharide as described herein, to a subject considered at risk of, or known to be exposed to coronavirus. Examples of subjects who may be at risk of exposure and infection include subjects who are immunocompromised (including a subject who has primary or secondary immunodeficiency), an adult more than 60 years of age, a child younger than 2 years of age, healthcare workers, adults or children in close contact with a person(s) with confirmed or suspected coronavirus infection, and people with underlying medical conditions such as pulmonary infection, heart disease, obesity or diabetes.

The methods of the present invention are also useful for reducing viral load in individuals who are asymptomatic, and thereby reduce the likelihood of the individual spreading the infection to other individuals. Non-symptomatic individuals may be identified via faecal, nasal and/or pharangeal swabs which indicate a presence of coronavirus infection.

In any aspect described herein, the sulfated polysaccharide is selected from the group consisting of: pentosan polysulfate, chondroitin sulfate A, chondroitin sulfate B, chondroitin sulfate C, keratan sulfate, heparin, heparan sulfate, dextran polysulfate, fucoidan, lentinan sulfate, mannan sulfate, galactan sulfate, xylomannan sulfate, rhamnan sulfate, curdlan sulfate, or sulfated fucan and pharmaceutically acceptable salts thereof.

In particularly preferred aspects of the present invention, the sulphated polysaccharide is pentosan polysulfate, or a pharmaceutically acceptable salt thereof.

In any embodiment of the invention, the sulfated polysaccharide, preferably pentosan polysulfate (PPS) is administered to the individual intravenously, subcutaneously, orally, intramuscularly, via gastric tube, intranasally or by inhalation.

The present invention also provides for the use of a sulfated polysaccharide, or a pharmaceutically acceptable salt thereof, in the manufacture of a medicament for:

- treating or preventing a coronavirus infection;
- reducing the severity of a coronavirus infection;
- treating and/or preventing a disease associated with, or caused by, a coronavirus infection;
- treating or preventing a respiratory disease, an inflammatory disease (including cytokine-associated toxicity), a cardiovascular disease or a gastrointestinal disease caused by or associated with a coronavirus infection;
- treating or preventing cytokine-associated toxicity caused by or associated with a coronavirus infection; and/or
- treating or preventing one or more of fever, hypotension, tachycardia, myalgia, headache or inappropriate cytokine release induced by coronavirus infection.

In any use described herein, the sulfated polysaccharide is optionally selected from the group consisting of: pentosan polysulfate, chondroitin sulfate A, chondroitin sulfate B, chondroitin sulfate C, keratan sulfate, heparin, heparan sulfate, dextran polysulfate, fucoidan, lentinan sulfate, mannan sulfate, galactan sulfate, xylomannan sulfate, rhamnan sulfate, curdlan sulfate, or sulfated fucan and pharmaceutically acceptable salts thereof. Preferably, the sulphated polysaccharide is pentosan polysulfate, or a pharmaceutically acceptable salt thereof.

In any use described herein, the coronavirus infection is an infection with a beta-coronavirus, preferably from an infection with a beta-coronavirus from Lineage B, such as an infection with SARS-CoV or an infection with SARS-CoV-2. Preferably, the coronavirus infection is a SARS-CoV-2 infection, or an infection with a mutated form or variant thereof, including but not limited to mutants D614G, S477N, 20A.EU1, or the Danish COVID-19 mink variant.

The present invention also provides for a sulfated polysaccharide, preferably pentosan polysulfate, or a pharmaceutically acceptable salt thereof, or a pharmaceutical composition comprising a sulphated polysaccharide, preferably pentosane polysulfate or a pharmaceutically acceptable salt thereof, for use in:

- treating or preventing a coronavirus infection;
- reducing the severity of a coronavirus infection;
- treating and/or preventing a disease associated with, or caused by, a coronavirus infection;
- treating or preventing a respiratory disease, an inflammatory disease (including cytokine-associated toxicity), a cardiovascular disease or a gastrointestinal disease caused by or associated with a coronavirus infection;
- treating or preventing cytokine-associated toxicity caused by or associated with a coronavirus infection; and/or
- treating or preventing one or more of fever, hypotension, tachycardia, myalgia, headache or inappropriate cytokine release induced by coronavirus infection.

As used herein, except where the context requires otherwise, the term "comprise" and variations of the term, such as "comprising", "comprises" and "comprised", are not intended to exclude further additives, components, integers or steps.

Further aspects of the present invention and further embodiments of the aspects described in the preceding paragraphs will become apparent from the following description, given by way of example and with reference to the accompanying drawings.

DESCRIPTION OF THE DRAWINGS

FIG. 1: Inhibition of SARS-CoV-2 replication by polysulfated polysaccharides. Data presented is inhibition by polysaccharide relative to control.

FIG. 2: M100 microscopy image of HCT116 cells fed FITC-NaPPS (green) then immunostained for Rab9 (red). Extensive cytoplasmic, perinuclear colocalization of the Rab9 with NaPPS was observed in HCT116 cells (arrows).

FIG. 3: M100 microscopy image of HCT116 cells fed FITC-NaPPS (green) then immunostained for TGN46 (red) a marker of the trans golgi network. TGN36 stained the trans golgi in classical cisternal morphology. NaPPS accumulation was observed in close proximity to edges of the trans golgi stacks. (arrows).

DETAILED DESCRIPTION OF THE EMBODIMENTS

It will be understood that the invention disclosed and defined in this specification extends to all alternative combinations of two or more of the individual features mentioned or evident from the text or drawings. All of these different combinations constitute various alternative aspects of the invention.

Reference will now be made in detail to certain embodiments of the invention. While the invention will be described in conjunction with the embodiments, it will be understood that the intention is not to limit the invention to those embodiments. On the contrary, the invention is intended to cover all alternatives, modifications, and equivalents, which may be included within the scope of the present invention as defined by the claims.

One skilled in the art will recognize many methods and materials similar or equivalent to those described herein, which could be used in the practice of the present invention. The present invention is in no way limited to the methods and materials described. It will be understood that the invention disclosed and defined in this specification extends to all alternative combinations of two or more of the individual features mentioned or evident from the text or drawings. All of these different combinations constitute various alternative aspects of the invention.

The present invention is based on the surprising finding by the inventor, that polysulfated polysaccharides are useful in reducing the severity coronavirus infection and can be used to treat diseases or conditions associated with, or caused by, coronavirus infection. In particular, the inventor has found that the polysulfated polysaccharide pentosan polysulfate (PPS) is significantly more effective at reducing replication of SARS-CoV-2 compared to other polysulfated polysaccharides and can therefore be used to reduce the severity of or prevent infection by SARS-CoV-2. The methods of the present invention are therefore also useful for reducing the likelihood of a subject developing severe disease and/or cytokine associated toxicity arising from infection with a coronavirus.

Coronavirus

"Coronavirus" as used herein refers to members of the subfamily Coronavirinae in the family Coronaviridae and the order Nidovirales (International Committee on Taxonomy of Viruses). This subfamily consists of four genera, Alphacoronavirus, Betacoronavirus, Gammacoronavirus and Deltacoronavirus, on the basis of their phylogenetic relationships and genomic structures. Subgroup clusters are labeled as 1a and 1b for the Alphacoronavirus and 2a, 2b, 2c, and 2d for the Betacoronavirus. The alphacoronaviruses and betacoronaviruses infect only mammals. The gammacoronaviruses and deltacoronaviruses infect birds, but some of them can also infect mammals. Alphacoronaviruses and betacoronaviruses usually cause respiratory illness in humans and gastroenteritis in animals. The three highly pathogenic viruses, SARS-CoV, MERS-CoV and SARS-CoV-2, cause severe respiratory syndrome in humans, and the other four human coronaviruses (HCoV-NL63, HCoV-229E, HCoV-OC43 and HKU1) induce only mild upper respiratory diseases in immunocompetent hosts, although some of them can cause severe infections in infants, young children and elderly individuals. Alphacoronaviruses and betacoronaviruses can pose a heavy disease burden on livestock; these viruses include porcine transmissible gastroenteritis virus, porcine enteric diarrhoea virus (PEDV) and the recently emerged swine acute diarrhoea syndrome coronavirus (SADS-CoV). On the basis of current sequence databases, all human coronaviruses have animal origins: SARS-CoV, MERS-CoV, SARS-CoV-2, HCoV-NL63 and HCoV-229E are considered to have originated in bats; HCoV-OC43 and HKU1 likely originated from rodents.

The coronaviruses include antigenic groups I, II, and III. Non-limiting examples of coronaviruses include SARS coronavirus, MERS coronavirus, transmissible gastroenteritis virus (TGEV), human respiratory coronavirus, porcine respiratory coronavirus, canine coronavirus, feline enteric coronavirus, feline infectious peritonitis virus, rabbit coronavirus, murine hepatitis virus, sialodacryoadenitis virus, porcine hemagglutinating encephalomyelitis virus, bovine coronavirus, avian infectious bronchitis virus, and turkey coronavirus, as well as any others described herein, and including those referred to in Cui, et al. Nature Reviews Microbiology volume 17, pages 181-192 (2019), and Shereen et al. Journal of Advanced Research, Volume 24, July 2020 (published online 16 Mar. 2020), Pages 91-98.

A subject or individual in need of treatment according to any aspect of the invention, or requiring administration of any composition described herein, may be an individual who is displaying a symptom of a coronavirus infection or who has been diagnosed with a coronavirus infection. Further, the subject or individual may be one who has been clinically or biochemically determined to be infected with a coronavirus (e.g., via sequencing of blood samples or sequencing or antibody-based approaches for detecting coronavirus in nasal and/or nasopharangeal swabs, or from a saliva-based assay).

A subject may be in a stage of coronavirus infection before end stage-organ failure has developed. A subject in need thereof may be anyone with a coronavirus infection from the onset of clinical progression, before end-organ failure has developed. In one embodiment, the subject has had coronavirus infection symptoms for less than or equal to 12 days, and who does not have life-threatening organ dysfunction or organ failure. Preferably the subject is early in the course of the disease, for example, before day 14 from symptom onset, or during the viremic and seronegative stage.

A subject may have recovered from symptoms or signs of infection but still be shedding or carrying viral particles. A subject may have "long COVID" and be presenting with signs or symptoms of a past coronavirus infection.

A "subject" or "individual" can also be any animal that is susceptible to infection by coronavirus and/or susceptible to diseases or disorders caused by coronavirus infection. A subject of this invention can be a mammal and in particular embodiments is a human, which can be an infant, a child, an adult or an elderly adult.

A "subject at risk of infection by a coronavirus" or a "subject at risk of coronavirus infection" is any subject who may be or has been exposed to a coronavirus. "Subject" or "individual" includes any human or non-human animal. Thus, in addition to being useful for human treatment, the compounds of the present invention may also be useful for veterinary treatment of mammals, including companion animals and farm animals, such as, but not limited to dogs, cats, horses, cows, sheep, and pigs, or any animal that can be infected by coronavirus.

Subjects at risk include, but are not limited to, an immunocompromised person, an elderly adult (more than 65 years of age), children younger than 2 years of age, healthcare workers, adults or children in close contact with a person(s) with confirmed or suspected coronavirus infection, and people with underlying medical conditions such as pulmonary infection, heart disease or diabetes, primary or secondary immunodeficiency.

Treatment of Coronavirus Infection and of Diseases and Conditions Associated with Coronavirus Infection Among the conditions associated with coronavirus infection, particularly infection with SARS-CoV-2, is an inappropriate or uncontrolled activation of the immune system, otherwise referred to as "cytokine storm" or "cytokine associated toxicity".

Inappropriate or uncontrolled activation of the immune system can result in a potentially fatal immune reaction consisting of a positive feedback loop between cytokines and white blood cells, with highly elevated levels of various cytokines. Such uncontrolled immune activation, often called a cytokine cascade, cytokine associated toxicity, cytokine release syndrome can be induced by a number of physical conditions or medical therapies, most notably immunotherapies which specifically exploit the immune system of the recipient to fight a disease. Cytokine storms have been demonstrated as a result of coronavirus infection.

Aberrant cytokine release may result from graft versus host disease (GVHD), avian influenza, smallpox, pandemic influenza, adult respiratory distress syndrome (ARDS), severe acute respiratory syndrome (SARS), sepsis, and systemic inflammatory response syndrome (SIRS). In fact, the cause of death in many of these conditions is not the pathology itself, but rather the effect of the cytokine cascade or storm that is induced as a result of the pathology. For example, cytokine storms are thought to be responsible for the disproportionate deaths of many healthy young adults during the flu pandemic of 1918. That is: the influenza wasn't the cause of death, but rather, the immune system's uncontrolled activation in response to the infection.

Although different terms may be used to describe cytokine storm, cytokine cascade or cytokine release syndrome, all of these conditions have in common the uncontrolled activation of the immune system, which can lead to potentially fatal consequences.

Current approaches for managing cytokine-associated toxicities involve the use of immunosuppressive agents, including monoclonal antibodies which bind IL-6, corticosteroids as well as vasopressors (such as noradrenaline, adrenaline and dopamine). A problem with this approach, however, is that in seeking to prevent or control cytokine-associated toxicity by immunosuppression, there is a risk of diminishing the efficacy of the immunotherapy.

Accordingly, there is a need for new approaches for treating or preventing cytokine-associated toxicity from immunotherapy, that facilitates or effectuates prevention, control, down-regulation, and/or termination of cytokine-associated toxicity, and which reduce or minimize a likelihood that undesirable side effects will occur.

The present inventor has surprisingly found that sulfated polysaccharides can be used to control the release of cytokines as a result of aberrant immune system activation, whether that activation arises as a result of coronavirus infection, avian influenza, smallpox, pandemic influenza, adult respiratory distress syndrome (ARDS), severe acute respiratory syndrome (SARS), sepsis, and systemic inflammatory response syndrome (SIRS).

Accordingly, in a first aspect, the present method relates to a method of treating coronavirus infection, including
  providing an individual who is suspected of having coronavirus infection,
  administering to the individual, an amount of a sulfated polysaccharide or a pharmaceutically acceptable salt thereof effective to treat the coronavirus infection
  thereby treating coronavirus infection in the individual.

The present invention also contemplates the use of sulfated polysaccharides as a means for preventing the onset of coronavirus infection in an individual, particularly where the individual is exposed to coronavirus.

Examples of pro-inflammatory cytokines or pro-inflammatory mediators include interleukin-1 alpha (IL-1 α) and interleukin-1-beta (IL-1β) (hereinafter collectively referred to as interleukin-1 or IL-1), interleukin-6 (IL-6), interleukin-8 (IL-8), interleukin-11 (IL-11), interleukin-12 (IL-12), interleukin-17 (IL-17), interleukin-18 (IL-18), tumor necrosis factor-alpha (TNF-α), interferon-gamma (IFN-γ), granulocyte-macrophage colony stimulating factor (GM-CSF), and transforming growth factor-beta (TGF-β). It will be appreciated by the skilled person that references to pro-inflammatory cytokines in most embodiments of the present disclosure can refer any one or more of pro-inflammatory cytokines known in the art, and including one or more of the above-listed examples of pro-inflammatory cytokines.

In some embodiments, the decrease in quantity of pro-inflammatory cytokines within the individual assists in preventing, controlling, down-regulating, and/or stopping the occurrence of a cytokine-associated toxicity in the individual.

In some embodiments, the use of sulfated polysaccharides in accordance with the methods of the present invention, affects an anti-inflammatory cytokine, anti-inflammatory mediator, or anti-inflammatory factor condition, for instance by facilitating or effectuating increase in a quantity of the anti-inflammatory cytokine, anti-inflammatory mediator, and/or anti-inflammatory factor within the living organism. Examples of anti-inflammatory cytokines, anti-inflammatory mediators, and/or anti-inflammatory factors include interleukin-2 (IL-2), interleukin-4 (IL-4), interleukin-13 (IL-13), and interferon-alpha (IFN-α). A person of skill in the art will understand that a reference to anti-inflammatory cytokines, anti-inflammatory mediators, and/or anti-inflammatory factors in most embodiments of the present disclosure can relate to any one or more of anti-inflammatory cytokines, anti-inflammatory mediators, and/or anti-inflammatory factors known in the art, which includes the above-listed examples.

In some embodiments of the present disclosure, the use of sulfated polysaccharide facilitates or effectuates a decrease in gene expression of one or more pro-inflammatory cytokines within the body. For example, in several embodiments, the administration of sulfated polysaccharide to the individual at risk or suspected of having a cytokine-associated toxicity facilitates or effectuates decrease in IL-1 gene expression of an immune cell (i.e. a cell that is involved in immune responses) of the body. Examples of immune cells include lymphocytes, phagocytic cells, fibroblasts, monocytes, neutrophils, and macrophages.

In some embodiments of the present disclosure, the administration of sulfated polysaccharide facilitates or effectuates a decrease in secretion or release of one or more pro-inflammatory cytokines by an immune cell within the body. For example, in several embodiments, the sulfated polysaccharide facilitates or effectuates a decrease in IL-1 release or secretion from the immune cell.

In numerous embodiments, the decrease in gene expression of the pro-inflammatory cytokine (e.g., gene expression of IL-1) results in the decrease of secretion of the pro-inflammatory cytokine (e.g., decrease secretion of IL-1) by the immune cell, and hence a lower quantity of pro-inflammatory cytokine (e.g., lower quantity of IL-1) within the body. The lower quantity of pro-inflammatory cytokines (e.g., IL-1) within the body facilitates or effectuates or provides an anti-inflammatory effect.

In some embodiments of the present disclosure, the administration of sulfated polysaccharide facilitates or effectuates an increase in gene expression of one or more anti-inflammatory cytokine within the body. For example, in several embodiments, sulfated polysaccharide facilitates or effectuates increased gene expression of IL-2 by the immune cells of the body. In some embodiments of sulfated polysaccharide facilitates or effectuates an increase in secretion or release of one or more anti-inflammatory cytokine by immune cells within the body. For example, in several embodiments, sulfated polysaccharide facilitates or effectuates increased secretion of IL-2 by the immune cells of the body.

In yet further embodiment, the increase in the gene expression of one or more anti-inflammatory cytokines (e.g., IL-2) results in the increased secretion of the one or more anti-inflammatory cytokines by the immune cells of the body, and therefore a higher quantity of anti-inflammatory cytokines within the body. The higher quantity of anti-inflammatory cytokines within the body facilitates or effectuates or provides an anti-inflammatory effect.

A reduction in coronavirus infection may be determined using any method known in the art or described herein, including measuring viral load in a sample from the subject after treatment and comparing it to viral load in a sample from the same subject before treatment. The sample may be any biological sample obtained from the subject, and may include blood, saliva, urine, faeces, nasal wash, sputum, and mucous secretions. The sample may be taken from the respiratory tract, preferably the upper respiratory tract, for example the nose or pharynx (i.e. throat).

The term 'respiratory disease' or 'respiratory condition' refers to any one of several ailments that involve inflammation and affect a component of the respiratory system including the upper (including the nasal cavity, pharynx and larynx) and lower respiratory tract (including trachea, bronchi and lungs). The inflammation in the upper and lower respiratory tract may be associated with or caused by viral infection.

A symptom of respiratory disease may include cough, excess sputum production, a sense of breathlessness or chest tightness with audible wheeze.

The existence of, improvement in, treatment of or prevention of a respiratory disease may be determined by any clinically or biochemically relevant method of the subject or a biopsy therefrom. For example, a parameter measured may be the presence or degree of lung function, signs and symptoms of obstruction; exercise tolerance; night time awakenings; days lost to school or work; bronchodilator usage; Inhaled corticosteroid (ICS) dose; oral glucocorticoid (GC) usage; need for other medications; need for medical treatment; hospital admission.

As used herein, the term respiratory infection means an infection by a coronavirus, preferably by SARS-CoV-2, anywhere in the respiratory tract.

An individual may be identified as having a respiratory tract infection by viral testing and may exhibit symptoms of itchy watery eyes, nasal discharge, nasal congestion, sneezing, sore throat, cough, headache, fever, malaise, fatigue and weakness. In one aspect, a subject having a respiratory infection may not have any other respiratory condition. Detection of the presence or amount of virus may be by PCR/sequencing of RNA isolated from clinical samples (nasal wash, sputum, BAL) or serology.

The terms "treatment" or "treating" of a subject includes the application or administration of polysulfated polysaccharide as described herein, with the purpose of delaying, slowing, stabilizing, curing, healing, alleviating, relieving, altering, remedying, less worsening, ameliorating, improving, or affecting the disease or condition, the symptom of the disease or condition, or the risk of (or susceptibility to) the disease or condition.

The term "treating" refers to any indication of success in the treatment or amelioration of an injury, pathology or condition, including any objective or subjective parameter such as abatement; remission; lessening of the rate of worsening; lessening severity of the disease; stabilization, diminishing of symptoms or making the injury, pathology or condition more tolerable to the subject; slowing in the rate of degeneration or decline; making the final point of degeneration less debilitating; or improving a subject's physical or mental well-being.

It will be appreciated that coronavirus infection may not necessarily lead to severe disease, such as cytokine storm. The present invention, therefore contemplates the use of sulfated polysaccharides for the treatment of any symptom of coronavirus infection, regardless of how mild or severe. Thus, the present invention includes methods of treating individuals who have relatively mild symptoms of infection, such as headache, fever, cough and fatigue. Such individuals will generally not require hospitalisation (and can be treated at home). Other individuals may have sufficiently severe symptoms that may require hospitalisation, although it will be appreciated that such individuals may not necessarily develop cytokine storm.

Further still, it is to be recognised that not all instances of coronavirus infection are symptomatic, including infection with SARS-CoV-2. However, given the findings of the present inventor, it will be appreciated that the methods of the invention find application in the treating of an infection (including to reduce viral load in the individual), even when the individual is asymptomatic. Such individuals may easily be identified through the use of routine screening of faecal, nasal and/or nasopharangeal swabs. Moreover, it will be appreciated that this approach reduces the likelihood of an individual spreading their infection to others, and consequently the methods of the invention can be extended to a method for reducing the likelihood of transmission of a coronavirus infection to another individual.

Given the breadth of symptoms caused by coronaviruses, (and range of severity thereof) including by SARS-CoV-2, it will be appreciated that a positive response to therapy according to the methods described herein, may include any amelioration or improvement of symptoms experienced by the subject.

For example, a positive response to therapy may be a reduction in general levels of fatigue, muscle pain, headache and/or lethargy in the subject. A positive response may also include a reduction in fever, and a return to afebrile state in the subject.

A positive response to therapy may also be prevention or attenuation of worsening of respiratory symptoms following a respiratory virus infection. This could be assessed by comparison of the mean change in disease score from baseline to end of study period, for example, based on a questionnaire, and could also assess lower respiratory symptom score (LRSS—symptoms of chest tightness, wheeze, shortness or breath and cough) daily following infection/onset of cold symptoms. Change from baseline lung function (peak expiratory flow PEF) could also be assessed and a positive response to therapy could be a significant attenuation in reduced PEF. For example, a placebo treated group would show a significant reduction in morning PEF of 15% at the peak of exacerbation whilst the treatment group would show a non-significant reduction in PEF less than 15% change from baseline.

A positive response to therapy may also be a reduction in the presence of ground-glass type opacities in the lung periphery or near the pleura (for example, as determined using chest CT imaging techniques).

A positive response to therapy may also include an increase or return to normal levels of blood oxygenation levels.

A positive response to therapy may also include an improvement in cardiovascular disorders such as alterations in blood pressure and increased presence of clotting factors.

The methods of the present invention can further be applied once an individual has recovered from an initial coronavirus infection. Such methods may find utility in the treatment of "long covid" symptoms, or in individuals who have long periods of viral particle excretion. The methods of the invention can also be utilised to prevent or reduce the likelihood of reinfection with coronavirus, including re-infection with SARS-CoV-2 (and variants thereof).

Sulfated Polysaccharides

As used herein, the term sulfated polysaccharide includes sulfated polysaccharides, sulfated oligosaccharides and glycosaminoglcans, including glycosaminoglycans linked to a core protein, such as heparin sulfate proteoglycans.

Non-limiting examples of sulfated polysaccharides include: pentosan polysulfate (PPS), chondroitin sulfate A, chondroitin sulfate B, chondroitin sulfate C, keratan sulfate, heparin, heparan sulfate, dextran polysulfate, fucoidan, lentinan sulfate, mannan sulfate, galactan sulfate, xylomannan sulfate, rhamnan sulfate, curdlan sulfate and sulfated fucan.

The invention also contemplates the use of various pharmaceutically acceptable salts of any one of the above mentioned sulfated polysaccharides, including but not limited to the sodium, calcium, potassium and magnesium salts.

Accordingly, in a further aspect, the present method relates to a method of treating cytokine-associated toxicity, including
- providing an individual who is suspected of having cytokine-associated toxicity,
- administering to the individual, an amount of a polysulfated polysaccharide or a pharmaceutically acceptable salt thereof effective to treat the cytokine-associated toxicity wherein the polysulfated polysaccharide is selected from the group consisting of pentosan polysulfate, chondroitin sulfate A, chondroitin sulfate B, chondroitin sulfate C, keratan sulfate, heparin, heparan sulfate, dextran polysulfate, fucoidan, lentinan sulfate, mannan sulfate, galactan sulfate, xylomannan sulfate, rhamnan sulfate, curdlan sulfate, or sulfated fucan.

The present invention also contemplates the use of molecular weight variations of any one of the sulfated polysaccharides described herein, including molecular weights ranging from 100 to 10,000,000 mass units, preferably 1,000 to 100,000 mass units, more preferably 1,800 to 9,000 mass units.

The skilled person will also appreciate that the degree of sulfation of the sulfated polyaccharides described herein may also vary. Varying degrees of sulfation occur in both naturally occurring and synthetic sulfated polysaccharides. The degree of sulfation of the sulfated polysaccharide may be preferably about 0.5, 0.6, 0.7, 0.8, 0.9, 1.0, 1.1, 1.2, 1.3, 1.4, 1.5, 1.6, 1.7, 1.8, 1.9, 2.0, or more than 2.0. In a preferred embodiment the invention relates to a sulfated polysaccharide for use as described herein, wherein the degree of sulfation of the polysaccharide is high, for example, 1.9.

Pentosan Polysulfate

In a particularly preferred embodiment of the present invention, the sulfated polysaccharide is pentosan polysulfate (PPS; also known as [(2R,3R,4S,5R)-2-hydroxy-5-[(2S,3R,4S,5R)-5-hydroxy-3,4-disulfooxyoxan-2-yl]oxy-3-sulfooxyoxan-4-yl] hydrogen sulfate) is a semi-synthetically derived heparin-like macromolecule carbohydrate derivative, which chemically and structurally resembles glycosaminoglycans (GAGs). There are 40 synonyms listed for pentosan polysulfate on PubChem including BAY-946, HOE-946, pentosan sulfuric polyester, polypentose sulfate, polysulfated xylan, PZ-68, SP-54, xylan SP54 and xylan sulfate. PPS is disclosed in U.S. Pat. No. 2,689,848 and this compound has been known since the early 1960s to be a synthetic heparinoid and an anti-thrombotic agent. PPS was originally developed as a heparin-like agent which interferes with the binding of factor Xa to thrombin via an AT-III independent mechanism. While having similar structural properties to heparin, PPS is more heavily sulfated and consequently has a greater overall negative charge. Further, PPS has only about $1/15$ the anticoagulant properties of heparin.

PPS is most commonly used as an oral formulation to treat interstitial cystitis in humans and as an injectable drug to treat osteoarthritis in companion animals (Fuller, Ghosh et al., "Plasma and synovial fluid concentrations of calcium pentosan polysulfate achieved in the horse following intramuscular injection," Equine Veterinary Journal (2002)). The compound PPS may also be used as an anticoagulant, preventing the formation of blood clots, although it has $1/15$ the anti-coagulant properties if heparin. PPS has also been used for treatment of hematomes, hemorrhoids, frostbites, burns, and multiparameter illnesses such as thrombosis and atherosclerosis.

In the context of interstitial cystitis, PPS is believed to provide a protective coating to the damaged bladder wall due to is similar structure with the natural glycosaminoglycan coating of the inner lining of the bladder. Thus, it is thought that PPS may replace or repair the lining of the bladder in interstitial cystitis, reducing its permeability.

The mechanism of PPS action in osteoarthritis is multifactorial, with both stimulation of cartilage matrix synthesis and prevention of cartilage breakdown. There are also systemic effects on blood lipids and fibrinolysis that may help clear the subchondral circulation.

PPS is obtained by sulfate esterification of beechwood (*Fagus sylvatica*) hemicellulose and consists of a mixture of polymers with molecular weight ranging from 1,800 to 9,000 mass units (mean 4,700 units). PPS is produced from a chemical solution of polysaccharides (e.g. Xylan) extracted from the bark of the beech tree or other plant sources which is then treated with sulfating agents such as chlorosulfonic acid or sulfuryl chloride and an acid. After sulfation, PPS is usually treated with sodium hydroxide to yield the sodium salt.

Various methods have been described for the preparation of PPS including WO/2008/107906, WO/2009/047699 and WO/2012/114349, the entire contents of which are herein incorporated by reference.

In some embodiments, the polysulfated polysaccharide for use in accordance with the methods of the present invention, is the sodium pentosan polysulfate manufactured to the specifications lodged with the US FDA and European Community EMEA by Bene-PharmaChem GmbH & Co KG, Geretsried, Germany.

In various embodiments, the molecular weight ranges as 100 to 10,000,000 mass units, preferably 1,000 to 100,000 mass units, more preferably 1,800 to 9,000 mass units.

The basic structure of PPS consists of pentoses, i. e. (1→4) linked beta-D-xylopyranose units containing glucuronic acid groups at statistically every 10th unit.

Below is the structural formula of pentosan polysulfate (PPS) isolated from beechwood hemicellulose. This formula shows that the linear xylan (pentosan) backbone of pentosan polysulfate contains on average one 4-0-methyl glucuronate side chain linked to the 2-position on every tenth xylose (pentose) ring.

The sodium derivative is when R=SO3Na. The calcium derivative of PPS (CaPPS) is when R=SO3Ca$^{+1}$ or SO3Ca$^{+2}$. The magnesium derivate of PPS (MgPPS) is when R=SO3Mg$^{+1}$ or SO3Mg$^{+2}$.

Pentosan polysulfate (PPS) is available as an alkali metal salt or alkaline earth metal salt, for example, comprising calcium or sodium salt, or transition metals such as copper and zinc and noble metals such as platinum. Accordingly, the particular complexing ions may be selected from the group consisting of the alkali metals, e.g. Na+ and alkaline earth metals, e.g. Ca2+, Zn2+, Mg2+, Ba2+, as well as Ag+, Pb2+, Cu2+, Au2+, Pd2+, Pd4+, Pd4+, Pd2+, trivalent metal ions, and quaternary ammonium compound complexes. Examples of the latter compound are pyridinium chloride, tetraalkyl ammonium chloride, chorine chloride, cetylpyridinium chloride, N-cetyl-N,N,N-trialkylammonium chloride or their derivatives. Preparation of the polysulfate polysaccharide-metal complexes is described in detail in U.S. Pat. No. 5,668,116, the entire disclosure of which is incorporated herein by reference.

Accordingly, in a yet further embodiment, the pharmaceutically acceptable salt of pentosan polysulfate used in the method of the present invention, is the sodium salt of pentosan polysulfate (NaPPS), the magnesium salt of pentosan polysulfate (MgPPS), and/or the calcium salt of pentosan polysulfate (CaPPS). Preferably, the sodium salt is used in the methods of the present invention.

In yet further embodiments, the present invention includes the use of pentosan polysulfate having varying degrees of sulfation. For example, the degree of sulfation may be from 0.2 to 2 sulfates per sugar moiety. In a preferred embodiment, the degree of sulfation may be 1.9 per sugar moiety.

The present invention also encompasses biologically active molecular fragments of PPS or analogues or derivatives of PPS.

A significant advantage of the present invention over the current approaches for treating cytokine-associated toxicity, is the well-known safety profile of PPS. Even when administered at high doses for extended periods, PPS has been reported to produce only limited side effects (Nickel et al., 2005). A further advantage is that PPS is bioavailable when administered orally, intravenously or subcutaneously (which is in contrast to other GAGs).

Cytokine Associated Toxicity

As used herein, cytokine-associated toxicity refers to a potentially life-threatening adverse cytokine response to aberrant immune system activation, for example caused by illness but also including an immunomodulating therapy.

Cytokine-associated toxicity is also described in the art using the term cytokine release syndrome (CRS). When sufficiently severe, this syndrome can be referred to as hypercytokinemia or 'cytokine storm'. As used herein, CRS defines a systemic inflammatory response in a patient inter alia characterized by hypotension, pyrexia and/or rigors, and potentially resulting in death. CRS is believed to be caused by an uncontrolled positive feedback loop between cytokines and immune cells, resulting in highly elevated levels of various cytokines. CRS also involves the systemic expression of immune system mediators and includes increased levels of pro-inflammatory cytokines and anti-inflammatory cytokines.

During a cytokine storm, inflammatory mediators, for example pro-inflammatory cytokines such as Interleukin-1 (IL1), Interleukin-6 (IL6), tumor necrosis factor-alpha (TNF-alpha), oxygen free radicals, and coagulation factors are released by the immune cells of the body. Cytokine storms have the potential to cause significant damage to body tissues and organs. For example, occurrence of cytokine storms in the lungs can cause an accumulation of fluids and immune cells, for example macrophages, in the lungs, and eventually block off the body's airways thereby resulting in respiratory distress and even death.

As described above, the present invention relates to a method of treating or preventing cytokine-associate toxicity (or adverse cytokine response). In certain embodiments, the cytokine-associated toxicity is sufficiently severe to be classified as a "cytokine storm" or hypercytokinemia. Accordingly, in a further embodiment, the present invention relates to a method of treating hypercytokinemia in an individual, including
  providing an individual at risk of or suspected of having hypercytokinemia,
  administering to the individual, an amount of sulfated polysaccharide, or a pharmaceutically acceptable salt thereof, effective to treat hypercytokinemia
  thereby treating hypercytokinemia in the individual.

The hypercytonokinemia may be induced by graft versus host disease (GVHD), acute respiratory distress syndrome (ARDS), sepsis, systemic inflammatory response syndrome (SIRS), severe viral infection, shock, pneumonia severe acute respiratory syndrome (SARS), or immunotherapy.

Accordingly, the method also provides for a method of treating hypercytokinemia induced by graft versus host disease (GVHD), acute respiratory distress syndrome (ARDS), sepsis, systemic inflammatory response syndrome (SIRS), severe viral infection, shock, pneumonia severe acute respiratory syndrome (SARS), or immunotherapy, in an individual, including
  providing an individual at risk of or suspected of having hypercytokinemia induced by graft versus host disease (GVHD), acute respiratory distress syndrome (ARDS), sepsis, systemic inflammatory response syndrome (SIRS), severe viral infection, shock, pneumonia severe acute respiratory syndrome (SARS), or immunotherapy.
    administering to the individual, an amount of sulfated polysaccharide, or a pharmaceutically acceptable salt thereof, effective to treat hypercytokinemia
  thereby treating hypercytokinemia in the individual.

Administration of Sulfated Polysaccharides

According to various embodiments of the present invention, the sulfated polysaccharide formulations are preferably administered to humans who are at risk or suspected of having coronavirus infection (including cytokine-associated toxicity associated therewith). However, it will be understood that, although this specification refers specifically to applications in humans, the invention is also useful for veterinary purposes. Thus in all aspects the invention is useful for domestic animals such as cattle, sheep, horses and poultry; for companion animals such as cats and dogs; and for zoo animals. Therefore, the general term "subject" or "subject to be/being treated" is understood to include all animals (such as humans, apes, dogs, cats, horses, and cows) that have an enhanced immune response, whether caused by immunotherapy or as the result of another condition.

The methods described herein may involve the use of topical and systemic formulations for oral, intravenous, intramuscular, intra-articular, or subcutaneous administration of the sulfated polysaccharides. Various other embodiments may be formulated to be administered by way of a transdermal patch, a cream, intravenous solution, eye drops, spray, liposomes or any other method of application and ingestion (including through the use of a gastric tube)

In further embodiments, the sulphated polysaccharides may be adapted for administration by inhalation, for delivery to the upper or lower respiratory tract, Including the nasal and nasopharangeal tracts.

According to some embodiments, liquid (e.g., aqueous) sulfated polysaccharide formulations may be administered via injection. In some embodiments, liquid formulations may be administered orally. In some embodiments, liquid formulations may not be terminally sterilized.

The formulations described herein can be further processed by known methods to produce a pharmaceutically acceptable composition. In certain instances, this may entail using a pharmaceutically acceptable carrier with any of the formulations described herein, whether that carrier is in a liquid or solid format. For example, the formulation can be further processed so as to be administered in any suitable liquid or powder form, such as by pill, capsule, liquid, liposome, lyophilized composition, hard or soft chewable tablet. The formulation may be administered, e.g., to a mammal, in one or more dosage forms. Dosage forms of the formulation may be administered in an amount effective to treat one or more diseases.

The term "administered" means administration of a therapeutically effective dose of the aforementioned composition including the respective cells to an individual. By "therapeutically effective amount" is meant a dose that produces the effects for which it is administered. The exact dose will depend on the purpose of the treatment, and will be ascertainable by one skilled in the art using known techniques. As is known in the art and described above, adjustments for systemic versus localized delivery, age, body weight, general health, sex, diet, time of administration, drug interaction and the severity of the condition may be necessary, and will be ascertainable with routine experimentation by those skilled in the art.

Formulations

Methods of preparing various formulations of sulfated polysaccharides will be within the purview of the skilled person. In particular, the skilled person will be familiar with preparing oral or injectable dosage forms, depending on the preferred mode of administration of sulfated polysaccharides.

In certain preferred embodiments, the methods of the invention involve use or administration of an oral formulation. Oral formulations may be capsules, for example hard gelatine capsules and may contain excipients such as microcrystalline cellulose and lubricants such as magnesium stearate. The sulfated polysaccharide may be present in an amount of 10 mg to 1 g, or preferably about 100 mg.

Various formulations in accordance with the present invention may comprise one or more of the foregoing components in any suitable concentration or amount. For example, the sulfated polysaccharide may be present in a concentration of about 25 mg/mL to about 750 mg/mL or preferably about 25 to about 500 mg/mL, or more preferably about 250 mg/mL. In another example, the sulfated polysaccharide may be present in a total amount of about 10 mg to about 5 g. Buffers, for example, including sodium citrate, citric acid, or other buffers, may be present in concentrations such as about 1 to about 100 mM. For example, in some embodiments, a buffer such as sodium citrate may have concentrations in the formulation of about 50 mM (14.7 mg/mL), or a buffer such as citric acid may comprise about 55 mM (about 10.5 mg/mL). EDTA may be present in concentrations such as about 0.01% to about 0.5% w/v, 0.1 mM to about 1 mM, about 0.25 mg/mL, or more preferably about 0.25% w/v.

Chelators may be present in concentrations such as about 0.1 to about 1 mM. Preservatives may be present in concentrations such as about 0.1% to about 1%. Antioxidants may be present in concentrations such as about 0.1 to 10 mM. Antioxidants may also be present in concentrations of about 0.02% w/v to about 5% w/v. Excipients (e.g., pharmaceutical excipients) may be present in any suitable concentration, e.g., concentrations of about 1 to about 90%.

In other embodiments of the invention, various formulations may comprise one or more of these components in any suitable concentration or amount. For example, the sulfated polysaccharide, for example, PPS, may be present in a concentration of about 25 mg/mL to about 500 mg/mL, or more preferably about 250 mg/mL. Buffers may be present in concentrations such as of about 0.005% to about 5% w/v. Sodium bisulfite may be present in concentrations such as about 0.01% to about 1% w/v, about 0.02% to about 1% w/v, 10 mg/mL, or more preferably about 1% w/v. (When added to formulation of the present invention, sodium metabisulfite can convert to sulfur dioxide and sodium bisulfite. In embodiments, between about 25% and almost all of the metabisulfite may, upon addition to formulations of the present invention, convert to sulfur dioxide and sodium bisulfite.)

EDTA may be present in concentrations such as about 0.01% to about 0.5% w/v, 0.1 mM to about 1 mM, about 0.25 mg/mL, or more preferably about 0.25% w/v. Sodium citrate may be present in concentrations such as about 0.1 to about 4% w/v, or more preferably about 1.47% w/v. Citric acid may be present in concentrations such as about 0.5% to about 2% w/v, or more preferably about 1.05% w/v. Antimicrobial agents such as methyl paraben may be present in concentrations such as about 0.05% to about 0.2% w/v, or about 1 mg/mL, or more preferably about 0.1% w/v.

The formulations of the present invention may be in a liquid, solid, or lyophilized form and may be formulated as an aqueous solution. The formulation may be in a solution having any suitable pH, such as a pH of about 4 to about 8. In some embodiments, the formulation may have a pH of about 7 to about 8. For example, the formulation may be in a solution having any suitable pH, such as a pH of about 4 to about 8. It should be appreciated by those of ordinary skill in the art that the formulations of the present invention may be lyophilized to create a lyophilized dosage form, using techniques apparent to one of ordinary skill in the art in light of this specification. In addition, lyophilized dosage forms may be formulated to comprise, after reconstitution, a dosage form of any of the formulations described herein.

An exemplary formulation may comprise one or more of the following: PPS in a concentration of about 25 to about 500 mg/mL; metabisulfite or bisulfite (e.g., sodium bisulfite) in a concentration of about 0.05% w/v to 5% w/v; one or more chelators in a concentration of about 0.01% w/v to about 0.5% w/v; one or more buffers in a concentration of about 0.005% w/v to about 5% w/v; one or more antioxidants in a concentration of about 0.02% w/v to about 1% w/v; one or more antimicrobial agents in a concentration of about 0.05% w/v to about 0.2% w/v hyaluronic acid; and glucosamine.

In some embodiments, sodium bisulfite may be present in concentrations such as about 10 mg/mL. EDTA may be present in concentrations such as about 0.25 mg/mL. Sodium citrate may be present in concentrations such as about 14.7 mg/mL. Citric acid may be present in concentrations such as about 10.5 mg/mL. Methyl paraben may be present in concentrations such as about 1 mg/mL.

In one example, the dosage form may comprise pentosan polysulfate (PPS) at a concentration of about 250 mg/mL; sodium bisulfite in a concentration of up to about 20 mg/mL; and EDTA at a concentration of about 0.25 mg/mL. The formulation may be stable in a pH range of about 6 to about 7.

An exemplary formulation may comprise PPS in a concentration of about 250 mg/mL; sodium bisulfite in a concentration of up to about 10 mg/mL; EDTA in a concentration of about 0.25 mg/mL; and methyl paraben in a concentration of about 1 mg/mL. The formulation may be stable in a pH range of about 5.8 to about 6.2.

Another exemplary formulation may comprise PPS in a concentration of about 250 mg/mL; sodium bisulfite in a concentration of up to about 10 mg/mL; EDTA in a concentration of about 0.25 mg/mL; and methyl paraben in a concentration of about 1 mg/mL. The formulation may be stable in a pH range of about 7.8 to about 8.2. In some embodiments, the pH of the formulation may be adjusted with 1% w/v sodium hydroxide.

In preferred embodiments, the PPS may be formulated in any dosage form, such as a liquid, e.g. for oral administration, or an injectable dosage, most preferably, for oral administration.

Oral dosage forms of PPS may comprise PPS in an amount of from 25 mg to about 250 mg; preferably about 100 mg to about 200 mg.

Oral dosage forms may be immediate release capsules or delayed release capsules.

Further examples of PPS formulations are described in WO/2007/123800, the entire contents of which are herein incorporated by reference.

Dosing

The skilled person will be able to readily determine the appropriate dose of sulfated polysacchairde required for prevention or treatment of cytokine-associated toxicity. It will be appreciated that the dose of sulfated polysaccharide required, will depend on the severity of the toxicity (for example, if the toxicity is considered mild cytokine release syndrome or more severe hypercytokinemia) and thus, the skilled person will determine the appropriate dose on a case by case basis. Further, the degree of toxicity will also be influenced by factors such as the severity of the disease causing the cytokine associated toxicity or the severity of the disease being treated with immunotherapy (and the dose of immunotherapy this being administered). In yet a further consideration, the dose of sulfated polysaccharide may be adjusted depending on whether the sulfated polysaccharide is intended for prophylactic (i.e., prevention) treatment of cytokine-associated toxicity or is intended following evidence of the individual suffering from immunotherapy induced cytokine-associated toxicity.

The sulfated polysaccharide formulations used in accordance with the methods of the present invention may be formulated for administration to a mammal, e.g., for oral or injectable administration, in any of the dose ranges described below. The injection may be intravenous, intramuscular or subcutaneous.

A dose of the sulfated polysaccaride formulations for use in the methods of the present invention, may comprise sulfated polysaccharide in an amount of about 0.001 to 100 mg/kg/day.

In a preferred embodiment, when the sulfated polysaccharide is PPS, the amount provided in an injectable dose is 10 mg to about 5 g or about 1 mg/kg to about 5 mg/kg, for example. In some embodiments, a dose of about 3 mg/kg may be administered via injection. In some embodiments, the amount of the dosage form comprises an amount sufficient to inject about 1 mg/kg to about 5 mg/kg of PPS at each injection.

In some embodiments, a dose of the PPS formulations described herein, e.g., a dose for oral administration, may comprise PPS in an amount of about 4 mg/kg to about 20 mg/kg. In some embodiments, a dose of about 10 mg/kg may be administered orally. In some embodiments, the amount of the liquid formulation comprises an amount sufficient to deliver an oral dose of about 1 mg/kg to about 50 mg/kg of PPS at each administration.

It should be appreciated that smaller doses may be appropriate for humans and small mammals, while larger doses may be appropriate for larger animals. A dosage amount may be based on the mass of the target subject. For example, a dosage may comprise about 3 mg per kg of body mass of the target subject, such as a human or a horse.

In certain embodiments, PPS is administered by continuous venous infusion at a dose of 2 mg/kg, 3 mg/kg, 4 mg/kg, 5 mg/kg, 6 mg/kg, 7 mg/kg, 8 mg/kg, 9 mg/kg, 10 mg/kg, 12 mg/kg, 15 mg/kg or 20 mg/kg for a period of 1-3 weeks.

In yet further embodiments, PPS is administered by subcutaneous injection at a dose of 2 mg/kg, 3 mg/kg, 4 mg/kg, 5 mg/kg, 6 mg/kg, 7 mg/kg, 8 mg/kg, 9 mg/kg, or 10 mg/kg. when administered subcutaneously, PPS is preferably administered once a day, every second day, three times a week, or once a week.

It will be appreciated by those of ordinary skill in the art that the dosage for a particular formulation depends in part on the salt of PPS in the formulation. For example, formulations comprising sodium PPS may have a different dosage than formulations comprising calcium PPS. Dosage calculations can be determined by those of skilled in the art by evaluating body weight, surface area, and species differences.

According to various embodiments of the present invention, doses may be administered in a variety of frequencies. The frequency of dosing will vary depending on the severity of the coronavirus infection, the disease or condition associated with coronavirus infection including associated cytokine-associated toxicity. For example, if it is intended for the sulfated polysaccharide to act as a prophylactic to prevent onset of cytokine-associated toxicity, or other disease or condition or symptom associated with coronavirus infection, it may be preferable to administer the sulfated polysaccharide throughout the duration of coronavirus infection and until such time as the patient no longer has active infection. Alternatively, if the sulfated polysaccharide is being used in response to the onset of cytokine-associated toxicity, then the treatment course may be over only a short period of time and until the symptoms of cytokine-associated toxicity are reduced.

Oral doses of the formulations described herein may be administered daily, about once every two or three days, about twice weekly, or weekly. Injectable doses, such as intramuscular, intraarticular, subcutaneous or intravenous dosages, may be administered about daily, about once every two or three days, about twice weekly, about weekly, about bi-weekly, about monthly, or in other administration frequencies. Such doses may be administered for time periods such as about four weeks to about five weeks, about two months, about six months, or other term of treatment.

Doses described herein may also be administered in pulse therapy, e.g., where doses are administered periodically (e.g., about every three days) for a period of time such as 1-3 months, then not administered for a period of time such as 1-3 months, and then administered again periodically (e.g., about daily or at some other appropriate interval) for a time period such as 1-3 months. Other dosage regimens are apparent to one of ordinary skill in the art in light of this specification.

It will be appreciated by those of ordinary skill in the art that a single dose of the formulations described herein, such as a single daily dose, may be administered in parts and/or at different times throughout a single day. For instance, a daily dose may be divided so that half is administered twice per day, e.g., half in the morning and half at night or administered three times in a single day.

Combination Treatment for Cytokine-Associated Toxicity

The present invention also contemplates the co-administration of sulfated polysaccharides with other agents for preventing or treating the onset of cytokine-associated toxicity. For example, in one embodiment, corticosteroids such as prednisolone, methylprednisolone or dexamethasone may be used in conjunction with sulfated polysaccharides for preventing or treating cytokine-associated toxicity.

In yet a further embodiment, an anti-IL-6 antibody may be used in conjunction with a sulfated polysaccharide for preventing or treating cytokine-associated toxicity. For example, the IL-6 antibody may be tocilizumab.

Treatments which specifically target TNF-α may also be used in conjunction with sulfated polysaccharide for preventing or treating cytokine-associated toxicity. Examples of suitable TNF-α inhibitors are etanercept and infliximab. Angiotensin-II receptor blockers (ARBs) and angiotensin converting enzyme (ACE) inhibitors may also be suitable for down regulating TNFα in the context of cytokine-associated toxicity including hypercytokinemia. Examples of suitable ARBs and ACE inhibitors include losartan, telmisartan, irbesartan, olmesartan, valsartan, perindopril, trandolapril, captopril, enalapril, lisinopril, and ramipril.

In yet further embodiments, the present invention also contemplates the prevention or treatment of cytokine-associated toxicity using a combination of sulfated polysaccharide and OX40-Ig (a fusion protein for preventing binding of the ligand OX40 to recently activated T cells).

EXAMPLES

Example 1: Polysulphated Polysaccharides Inhibit Replication of Coronavirus

Materials
cell culture medium: DMEM F12+10% FCS+penstrep.
infection culture media: DMEM+TPCK trypsin+penstrep. (serum free);
Calu-3 cells (human lung cancer cell line)

| Polysulfated polysaccharides: Name | Av MW (Da) | Manufacturer | Cat. No. |
| --- | --- | --- | --- |
| Fondaparinux | (pentasaccharide) | S-Aldrich | SML1240 |
| Heparan sulfate | >25,000 | S-Aldrich | H7640 |
| Pentosan polysulfate | | Bene | |
| Dextran sulfate | 5,000 | S-Aldrich | 31404 |
| Pentosan polysulfate | | Manufacturer 2 | |
| Chondroitin sulfate A | | S-Aldrich | C9819 |

Experiments were conducted as follows:
Calu3 cells were treated pre- or post-infection with the polysulfated polysaccharides at 10 concentrations (or vehicle).
Cells were mock-infected or infected with SARS-CoV-2.
Viral loads were analysed at 1 time point by TCID50 assay, measuring cytopathic effect induced following serial passage of supernatant on target Vero cells.
Experiments were conducted in 96-well plates, consisting of 2 biological replicates, with a replicate consisting of 1× uninfected and 2× infected plates (pre+post), each as 60 wells/test compound/cell type (as 10 compound dilutions; sextuplicate technical replicates)+6 wells/control (pos+neg; single dilution). Compound were tested in this format on the same plate as a pre- or post-infection treatment.

Examplary Protocol
On Day 0, Calu cells were seeded in flat bottom 96 well plates in cell culture medium.

On Day 1: cells were infected with SARS-CoV-2. Briefly, 0.1 MOI SARS-CoV-2 was diluted in infection culture medium, applied to cells and then allowed to adsorb for 30 min. at 37° C., 5% $CO_2$. Diluted polysulfated polysaccharides or negative control (vehicle) were then applied to the infected cells. Polysulfated polysaccharides were added at a final concentration of between about 0.03 μM to about 55

µM. Cells were incubated in the presence of the polysulfated polysaccharides at 37° C., 5% $CO_2$ for 2 days.

On Day 4, samples of Calu culture media were obtained for the purposes of determining TCID50 (Median Tissue Culture Infectious Dose). Briefly, Calu culture medium was diluted in serum free DMEM in round bottom plates and then plated onto confluent layers of Cero cells (6 replicates per dilution). Cells were then incubated at 37° C., 5% $CO_2$ for 3 days.

On Day 7, the cytopathic effect (CPE) was calculated in order to determine TCID50/ml.

Results

Each concentration of drug treatment was scored for cytopathic effect and the results analysed by Spearman-Karber matrix.

Figure 1:
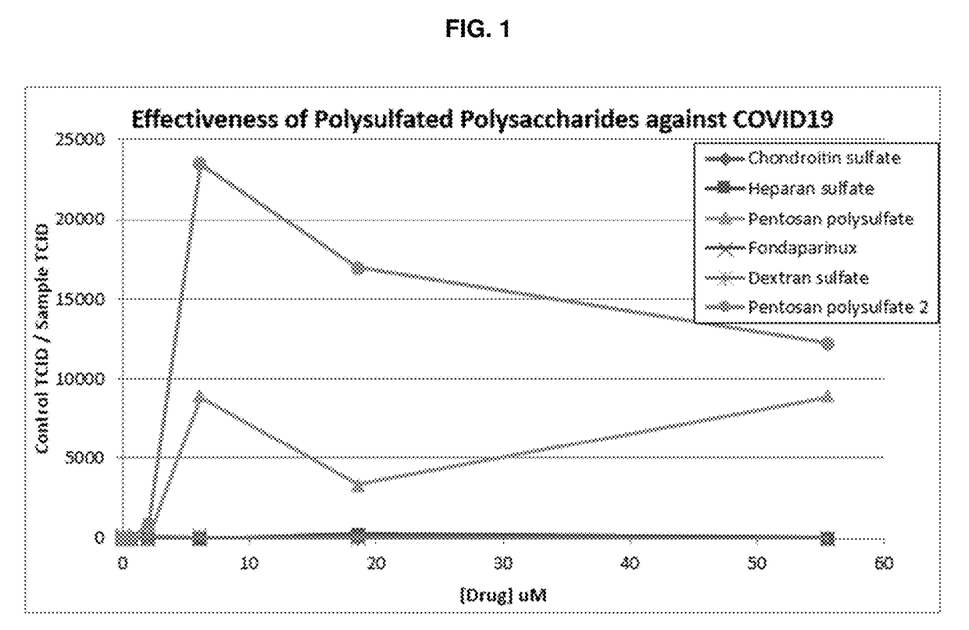
Figure 2:
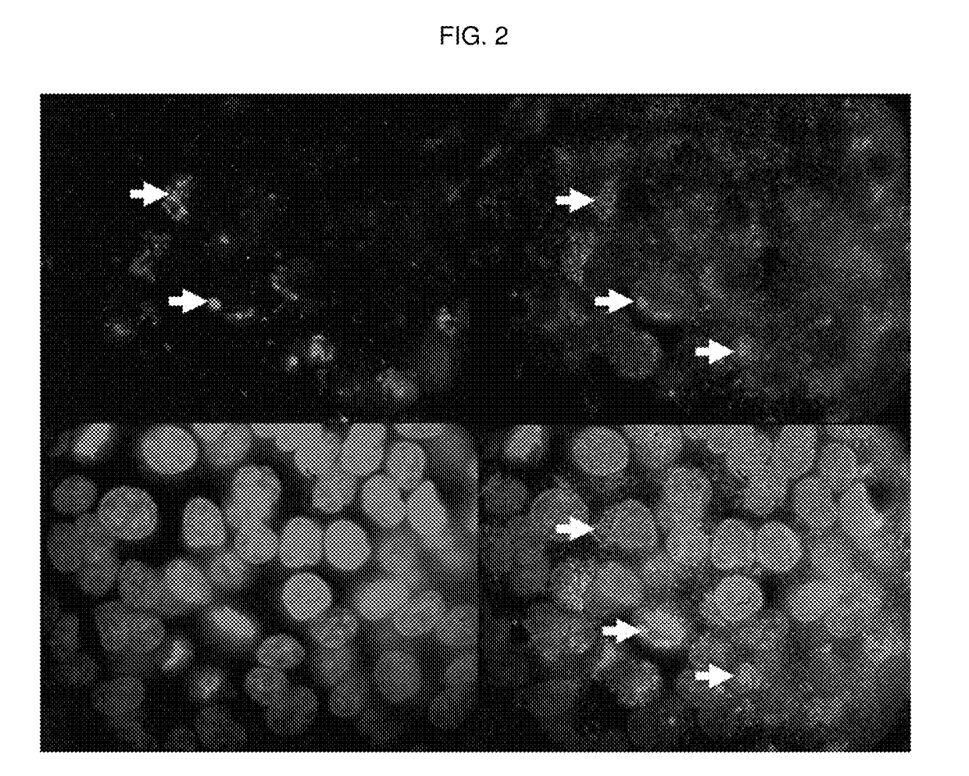
Figure 3:
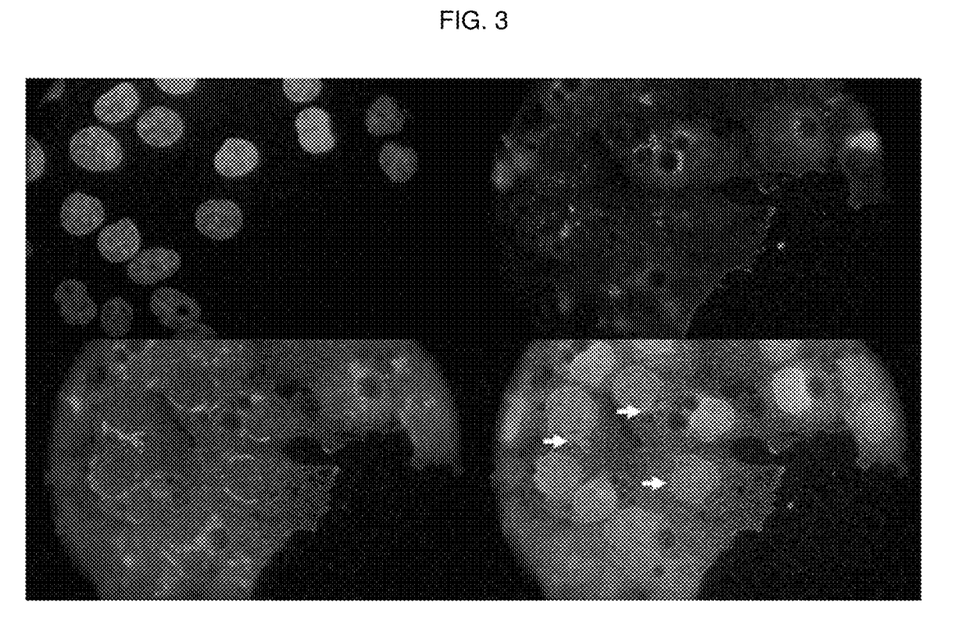

As shown in FIG. 1, virus replication in Calu3 cells was inhibited much more strongly with PPS compared with other polysulfated polysaccharides tested. This was measured by using the supernatant from the treated Calu3 cells in Vero cells, which undergo prominent cytopathic effect (CPE), which was then scored. Wells were scored 4 days after receiving supernatant as either positive (CPE) or negative (no virus). Tissue Culture Infectious Dose 50% (TCID50/mL) was calculated using the Spearman and Kärber test. Pentosan polysulfate (PPS) demonstrated an almost four orders of magnitude reduction in virus infectivity in the Calu3 SARS-CoV-2 in vitro model.

These results demonstrate that PPS inhibits SARS-CoV-2 viral replication and reduces viral infectivity and therefore suggests that PPS would be a useful therapeutic for the treatment of infection with SARS-CoV-2.

Example 2: PPS Inhibits Intracellular SARS-CoV-2 Assembly in Golgi and Golgi-Associated Compartments The SARS-COV-2 virus is known to enter cells via endosomes and then exploit the autophagy pathway of the host cell. There is accumulating evidence that endocytosed virus can interfere with the endogenous function of the autophagy-lysosome pathway and then replicate in autophagosome-like structures.

Autophagy has both canonical and non-canonical pathways. The latter utilizes autophagosomes derived from the trans-Golgi and late endosomes associated with small GTPase Ras-related protein Rab9.

In this study fluorescently labelled NaPPS was added to a culture of HCT116 colorectal carcinoma cells in vitro. Immunohistochemical staining was then used to compare the subcellular distribution of exogenous NaPPS and endogenous Rab9 endosomes.

Methods

Fluorescent tags were covalently bound to NaPPS after conversion to the ethyl-amino derivative followed by coupling with isothiocyanate ester of fluorescein using standard methods.

HCT116 cells were cultured on glass coverslips in DMEM with 20% fetal bovine serum and antibiotics (pen/strep) at 37° C., 5% $CO_2$ and 5% humidity. Cultures at 20-40% confluence were supplemented with 50 μg/ml FITC-NaPPS for 48h. Cells were then fixed with 4% paraformaldehyde in PBS then washed and incubated for 3h with a mouse antibody specific to Rab9 or TGN46 (a trans golgi marker) (2 μg/ml), then washed and stained with a goat-anti-mouse IgG antibody-coupled to Alexafluor 594. Samples were washed then counter stained with 0.5 μg/ml DAPI. Coverslips were mounted on slides and viewed at m200-m1000 on an Olympus BH2 fluorescence trinocular microscope using a HbO lamp and dichroic band-pass filter cubes. Images were captured to hard drive by a Jenoptik Gryphax camera and rendered using Adobe Photoshop software for contrast enhancement and edge sharpening.

Results

Extensive co-localization of Rab9 and FITC-NaPPS was observed in the cytoplasm of interphase and mitotic cells (FIG. 2). TGN46 staining revealed that NaPPS accumulated in endosomes close to the edges of the golgi stacks (FIG. 3).

CONCLUSIONS

These data provide evidence of a potential mechanism by which NaPPS reduces viral infectivity and replication. NaPPS is likely to be an effective treatment against SARS-COV-2 infection by specifically targeting the autophagosome compartment and other golgi compartments used by the virus for assembly.

It will be understood that the invention disclosed and defined in this specification extends to all alternative combinations of two or more of the individual features mentioned or evident from the text or drawings. All of these different combinations constitute various alternative aspects of the invention.

The invention claimed is:

1. A method of treating coronavirus infection or a disease or condition caused by or associated with coronavirus infection, the method comprising:

providing an individual who is suspected of having or of having had a coronavirus infection, administering to the individual, a therapeutically effective amount of pentosan polysulfate (PPS) or a pharmaceutically acceptable salt thereof thereby treating or preventing coronavirus infection or a disease or condition caused by or associated with coronavirus infection in the individual.

2. The method of claim 1, wherein the disease or condition caused by or associated with coronavirus infection is a respiratory disease or condition, an inflammatory disease or condition, a cardiovascular disease or condition or a gastrointestinal disease or condition.

3. The method of claim 1, wherein the disease or condition caused by or associated with coronavirus infection is cytokine-associated toxicity.

4. The method of claim 1, wherein the disease or condition is characterised as a mild condition that does not require hospitalisation.

5. The method of claim 1, wherein the disease or condition is characterised as severe and requiring hospitalisation.

6. The method of claim 1, wherein the individual does not display symptoms of coronavirus infection.

7. A method of preventing cytokine-associated toxicity induced by coronavirus infection, the method comprising:

providing an individual who been exposed to or has or is recovering from a coronavirus infection, administering to the individual, a therapeutically effective amount of pentosan polysulfate (PPS)_or a pharmaceutically acceptable salt thereof;

thereby preventing cytokine-associated toxicity in the individual.

8. The method according to claim 7, wherein the cytokine associated toxicity is characterised by one or more of fever, hypotension, tachycardia, myalgia, headache and elevated levels of one or more cytokines selected from the group consisting of: IL-1B, IL-2, IL-4, IL-5, IL-6, IL-7, IL-10, IL-12, IL-13, IL-17 INFγ, TNF-α, and granulocyte macrophage colony-stimulating factor.

9. The method of claim 1, wherein the method comprises treating one or more of fever, hypotension, tachycardia, myalgia, headache or inappropriate cytokine release induced by coronavirus infection.

10. The method of claim 1, wherein the pentosan polysulfate (PPS) is administered prior to or after the onset of coronavirus infection.

11. The method of claim 1, wherein the PPS is administered prophylactically once the individual has recovered from an initial infection with coronavirus.

12. A method of preventing or reducing the likelihood of coronavirus infection in an individual, the method comprising:
providing an individual who is at risk of infection with a coronavirus;
administering to the individual, a prophylactically effective amount of pentosane polysulfate (PPS), or a pharmaceutically acceptable salt thereof,
thereby preventing or reducing the likelihood of coronavirus infection in an individual.

13. The method of claim 12, wherein the method reduces the likelihood of serious coronavirus infection.

14. The method of claim 12, wherein the individual at risk is selected from: immunocompromised individuals, an adult more than 60 years of age, a child younger than 2 years of age, healthcare workers, adults or children in close contact with a person(s) with confirmed or suspected coronavirus infection, and people with underlying medical conditions such as pulmonary infection, heart disease, obesity or diabetes.

15. The method of claim 1, wherein the pentosan polysulfate (PPS) is administered to the individual intravenously, subcutaneously, orally, intramuscularly, via gastric tube, intranasally or by inhalation.

16. The method of claim 1, wherein the pentosan polysulfate is provided as a salt selected from the group consisting of sodium pentosan polysulfate, calcium pentosan polysulfate, and magnesium pentosan polysulfate.

17. The method of claim 1, wherein the coronavirus infection is an infection with SARS-CoV or SARS-CoV-2, or a mutated form or variant thereof.

18. The method of claim 1, wherein the coronavirus infection is an infection with SARS-CoV-2 or variant or mutated form thereof.

19. The method of claim 1, wherein the method includes further administering to the individual one or more of: a corticosteroid, an IL-6 inhibitor, a TNF-α inhibitor or a vasopressor.

20. The method of claim 3, wherein the cytokine-associated toxicity is hypercytokinemia.

21. The method of claim 14, wherein the immunocompromised individual is an individual who has primary or secondary immunodeficiency.

22. The method of claim 17, wherein the mutated form or variant thereof is mutant D614G, S477N, 20A.EU1, the Danish COVID-19 mink variant, the "UK" variant B 1 1 7, the "South African" variant B 1 351, the "Brazil" variant P1 or the "Russian" variant B 1 1 317.

* * * * *

UNITED STATES PATENT AND TRADEMARK OFFICE
CERTIFICATE OF CORRECTION

PATENT NO. : 11,938,146 B2
APPLICATION NO. : 18/071800
DATED : March 26, 2024
INVENTOR(S) : Sydney David Cullis-Hill It is certified that error appears in the above-identified patent and that said Letters Patent is hereby corrected as shown below:

In the Claims

Column 24, Claim 1, Line 35, delete "thereof" and replace with -- thereof, --

Column 24, Claim 7, Line 56, delete "who been" and replace with -- who has been --

Column 25, Claim 8, Line 1, delete "IL-17 INFγ," and replace with -- IL-17, INFγ, --

Column 26, Claim 22, Line 27, delete "B 1 1 7," and replace with -- B. 1. 1. 7, --

Column 26, Claim 22, Line 28, delete "B 1 351," and replace with -- B. 1. 351, --

Column 26, Claim 22, Line 28, delete "P1" and replace with -- P.1 --

Column 26, Claim 22, Line 29, delete "B 1 1 317." and replace with -- B. 1. 1. 317. --

Signed and Sealed this
Twenty-fifth Day of June, 2024

Katherine Kelly Vidal
*Director of the United States Patent and Trademark Office*